United States Patent [19]

Duan

[11] Patent Number: 5,225,473

[45] Date of Patent: * Jul. 6, 1993

[54] PRESSURE-SENSITIVE ADHESIVES

[75] Inventor: Daniel C. Duan, St. Paul, Minn.

[73] Assignee: Minnesota Mining and Manufacturing Company, St. Paul, Minn.

[*] Notice: The portion of the term of this patent subsequent to Jul. 18, 2006 has been disclaimed.

[21] Appl. No.: 866,207

[22] Filed: Apr. 9, 1992

Related U.S. Application Data

[63] Continuation of Ser. No. 642,147, Jan. 15, 1991, abandoned, which is a continuation of Ser. No. 125,406, Nov. 25, 1987, abandoned.

[51] Int. Cl.⁵ ............................................. C08K 5/05
[52] U.S. Cl. .................................. 524/388; 524/548; 522/79; 522/84; 522/167; 523/105
[58] Field of Search ................... 524/388, 548; 522/79, 522/84, 167; 523/105

[56] References Cited

U.S. PATENT DOCUMENTS

| | | | |
|---|---|---|---|
| 3,096,202 | 7/1963 | De Groot Von Arx | 117/68.5 |
| 3,252,995 | 5/1966 | Grosser et al. | 260/326.5 |
| 3,294,765 | 12/1966 | Hort et al. | 260/30.3 |
| 3,345,320 | 10/1967 | Uffner et al. | 260/31.6 |
| 3,532,679 | 10/1970 | Steckler | 260/80.72 |
| 3,689,439 | 9/1972 | Field et al. | 260/2.5 N |
| 3,759,880 | 9/1973 | Hoffmann et al. | 260/80.3 R |
| 3,907,720 | 9/1975 | Field et al. | 260/2.5 R |
| 3,925,282 | 12/1975 | Davis et al. | 260/23 H |
| 4,066,078 | 1/1978 | Berg | 128/2.06 E |
| 4,273,135 | 6/1981 | Larimore et al. | 128/640 |
| 4,352,359 | 10/1982 | Larimore et al. | 128/640 |
| 4,364,972 | 12/1982 | Moon | 427/54.1 |
| 4,524,087 | 6/1985 | Engel | 472/2 |
| 4,536,554 | 8/1985 | Lim et al. | 526/264 |
| 4,539,996 | 9/1985 | Engel | 128/640 |
| 4,554,924 | 11/1985 | Engel | 128/640 |
| 4,699,146 | 10/1987 | Sieverding | 128/640 |
| 4,750,482 | 6/1988 | Sieverding | 128/156 |
| 4,904,247 | 2/1990 | Therriault et al. | 604/304 |
| 4,931,282 | 6/1990 | Asmus et al. | 424/448 |

FOREIGN PATENT DOCUMENTS

| | | |
|---|---|---|
| 0107376 | 9/1983 | European Pat. Off. |
| 0238050 | 9/1987 | European Pat. Off. |
| WO86/05083 | 9/1986 | PCT Int'l Appl. |
| 1511563 | 6/1975 | United Kingdom |
| 2115431 | 2/1983 | United Kingdom |

*Primary Examiner*—Joseph L. Schofer
*Assistant Examiner*—R. H. Delmendo
*Attorney, Agent, or Firm*—Gary L. Griswold; Walter N. Kirn; John H. Hornickel

[57] ABSTRACT

Hydrophilic, cohesive, pressure-sensitive adhesive compositions are provided comprising a) a crosslinked, swellable polymeric matrix made from an N-vinyl lactam monomer and a multi-ethylenically unsaturated compound, wherein the ethylenic groups are vinyl groups, allyl groups, and/or methallyl groups, which groups are bonded to nitrogen or oxygen atoms, and b) a plasticizer for the copolymer wherein the amount of the multi-ethylenically unsaturated compound and the plasticizer are present in amounts sufficient to render the polymeric matrix cohesive, swellable and pressure-sensitive adhesive. These compositions can also be used as adhesives for biomedical electrodes and transdermal drug delivery systems.

9 Claims, 1 Drawing Sheet

PRESSURE-SENSITIVE ADHESIVES

This is a continuation of application Ser. No. 07/642,147, filed Jan. 15, 1991, abandoned, which is a continuation of application Ser. No. 07/125,406, filed Nov. 25, 1987, abandoned.

FIELD OF THE INVENTION

This invention relates to compositions comprised of a crosslinked hydrophilic polymer which compositions are useful as pressure-sensitive adhesives. One aspect of this invention relates to such compositions which have been made electrically-conductive for use as the skin interfacing material in a disposable bioelectrode. In its preferred embodiment, the invention relates to pressure sensitive adhesives made with N-vinyl-2-pyrrolidone crosslinked with controlled amounts of specific crosslinkers.

BACKGROUND OF THE INVENTION

Adhesives that tolerate incorporation of substantial amounts of water or other polar liquids without unacceptable phase separation, loss of tack, or loss of cohesive strength are needed for a variety of applications. Such an adhesive if made electrically conductive would have particular utility in biomedical electrodes. An adhesive that can be made electrochemically reactive and used with galvanically inert graphite conductors to make a bioelectrode that can recover from polarizing overloads is not known.

Many medical adhesives are known. Exemplary classes are polyvinyl ethers and copolymers of hydrophobic water insoluble monomers such as isooctyl acrylate and a small amount of a water soluble monomer such as a short chain $\alpha,\beta$-unsaturated carboxylic acid (e.g. acrylic acid) or an N-vinyl lactam (e.g. N-vinyl-2-pyrrolidone). While those formulations make excellent medical adhesives, incorporation of substantial amounts of ionic or highly polar solutions results in phase separation.

Conductive adhesives have been known for many years. U.S. Pat. No. 4,066,078 (to Berg), U.S. Pat. Nos. 4,273,135 and 4,352,359 (both to Larimore et al.) and U.S. Pat. Nos. 4,524,087, 4,539,996 and 4,554,924 (all to Engel) are representative. Berg discloses two classes of conductive adhesive plasticized with a polyhydric alcohol. One is a polymer or copolymer derived from the polymerization of an ester of an olefinically unsaturated carboxylic acid and a mono- or polyhydric alcohol having a terminal quaternary ammonium group. The second is sulfated cellulose esters. The procedures for making both classes are cumbersome with multiple steps.

The Larimore et al. patents each show three classes of polymers for use in conductive adhesives. U.S. Pat. No. 4,273,135 describes the first class which is comprised of non-ionic water soluble homo- or copolymers of substantially all water soluble monomers. The second and third classes are copolymers of water soluble monomers' and water insoluble monomers with the third class requiring the polymer to be water insoluble and at least 15% of the carboxylate containing monomers are required. While the electrical properties of these adhesives are suitable for some applications, no crosslinking is disclosed. Crosslinking allows for higher amounts of polyhydric alcohol without reducing viscosity below acceptable levels.

Two of the Engel patents (U.S. Pat. Nos. 4,524,087 and 4,539,996) disclose an electrically conductive adhesive formed by an essentially solventless free radical polymerization of an adhesive precursor having a polyhydric alcohol, at least one ionic monomer, a cross linker and an initiator. The ionic monomers listed are salts of $\alpha,\beta$-unsaturated carboxylic acids. The third Engle patent (U.S. Pat. No. 4,554,924) discloses a conductive adhesive formed by an essentially solventless free radical polymerization of an adhesive precursor having a polyhydric alcohol, at least one non-ionic monomer, an initiator, a crosslinker, and an ionizable salt present in an amount sufficient to render the composition electrically conductive. One of the examples describes a precursor comprising 115 g N-vinyl-2-pyrrolidone, 0.3 g triethylene glycol-bis-methacrylate, benzildimethylketal (Irgacure TM 651, Ciba Geigy), 25.0 g water, 250 g glycerol, 17.1 g potassium chloride, and 36.0 g polyacrylic acid solution (sodium salt in water (50% by weight)). The resultant adhesive has high tack, but is stringy, displaying poor cohesion so that upon removal it leaves a substantial residue.

The preferred Engel adhesives are used in a variety of biomedical electrodes. These adhesives are lightly crosslinked polymers of acrylic acid in glycerol with water and potassium chloride. While they have excellent properties for some applications, optimization of the electrical properties without adversely affecting adhesion properties has not been possible. Experience has shown that increasing the water content of the composition substantially improves the electrical properties of electrodes coated with the adhesive. Unfortunately increasing the water content to optimum levels for electrical performance is found to decrease the initial tack and cohesive strength of the polymer resulting in poor skin adhesion and residue when the electrode is removed. While tackifiers may be used, they have not been found particularly helpful in optimizing the electrical and adhesive properties. Additionally, prolonged storage (in excess of 2 years) results in loss of tack. This is believed to result from esterification crosslinking of polymeric chains.

Another conductive adhesive is disclosed in U.K. Patent Application No. 2,115,431. The adhesive comprises at least one irradiation cross-linked synthetic organic polymer and an adhesive plasticizer. The crosslinked polymer is formed by subjecting a solution or dispersion of at least one uncrosslinked synthetic organic polymer (including one which has repeating units derived from an N-vinyl lactam monomer) in a solubilizing plasticizer to ionization radiation energies of at least the equivalent of 100,000 electron volts (e.g., x-ray, gamma ray, and electron beam irradiation). Those skilled in the art will appreciate that while the use of ionizing irradiation to force chemical reactions can be useful for many applications, the use of ionizing irradiation is not always desirable because of the wide variety of reactive species that can be produced making the process very difficult to control and making the effect of additional constituents very difficult to predict.

Another art involving polymeric matrices that are swelled in water is the hydrogel art. These compositions are covalently crosslinked and are used extensively in contact lenses. Many of these hydrogels are based on poly(N-vinyl-2-pyrrolidone) and have been extensively used in medical applications. Because of the long experience with use of poly(N-vinyl-2-pyrrolidone) in medical applications its safety is well known making it a desirable candidate for biocompatible adhesives. While most hydrogels are not adhesive, EPO Appln. No. 83305770.6 (publication 0107376, 02/05/84) describes a hydrogel which has some tack and is recommended for use as a wound dressing. The hydrogel is prepared by dissolving between 5% and 25% by weight poly(N-vinyl-2-pyrrolidone) in water and crosslinking with ionizing irradiation (1 to 5 Mrads, electron beam). Here again the ionizing radiation process is not desirable.

Polymeric matrices using multifunctional monomers to crosslink N-vinyl lactams are known in the patent literature. None, however, have been found to be adhesive.

U.S. Pat. No. 3,294,765 discloses crosslinked polymeric matrices of N-vinyl lactams crosslinked with 3,3'-ethylidene-bis(N-vinyl-2-pyrrolidone). The patent indicates that polymeric matrices with mechanical properties ranging from thickened solutions to intractable gels are obtained depending on the relative amount of crosslinker used. None are reported to be adhesive.

U.S. Pat. No. 4,536,554 discloses polymeric network mixtures of polymers formed from hydrophilic monomer N-vinyl-2-pyrrolidone and hydrophobic monomer (5-alkylene-m-dioxanyl)acrylic ester. Crosslinkers identified as suitable for N-vinyl-2-pyrrolidone include 3,3'-ethylidene-bis(N-vinyl-2-pyrrolidone) and a variety of other diallyl, dimethallyl, and divinyl multifunctional monomers. As the polymeric networks are used for contact lenses adhesive characteristics would not be desirable.

The polymeric compositions known in the art have not met the need for an N-vinyl lactam based pressure sensitive adhesive that tolerates the incorporation of water and other polar liquids (particularly glycerol). A need continues to exist for an adhesive suitable for use in biomedical electrodes that will continue to function after prolonged storage. A need also exists for an adhesive that presents no biocompatibility problems and can be manufactured with straightforward processing.

SUMMARY OF THE INVENTION

Surprisingly, partially swelled gels derived from an N-vinyl lactam and suitable crosslinkers are found to form excellent pressure-sensitive adhesives which tolerate incorporation of substantial amounts of water and other polar liquids and ionic species. The present invention is a hydrophilic, pressure-sensitive adhesive composition comprising a crosslinked cohesive swellable polymeric matrix and a plasticizing solution. The crosslinked cohesive, swellable polymeric matrix is formed from free radical polymerization of a precursor having monomeric species and a crosslinker. When the majority of the monomeric species is an N-vinyl lactam the resultant adhesive tolerates substantial amounts of polar liquids and ionic species. While a number of crosslinkers can be used to crosslink N-vinyl lactams, the present invention uses a multi-ethylenically unsaturated compound wherein the ethylenic groups are vinyl, allyl, or methallyl groups bonded to nitrogen or oxygen atoms. The crosslinker and plasticizer are present in controlled amounts sufficient to yield a pressure sensitive adhesive swellable matrix.

The N vinyl lactam which comprises a majority of the monomeric portions of the precursor can be selected from the following illustrative group: N-vinyl-2-pyrrolidone; 5-methyl-N-vinyl-2-pyrrolidone; 5-ethyl-N-vinyl-2-pyrrolidone; 3,3-dimethyl-N-vinyl-2-pyrrolidone; 3-methyl-N-vinyl-2-pyrrolidone; 3-ethyl-N-vinyl-2-pyrrolidone; 4-methyl-N-vinyl-2-pyrrolidone; 4-ethyl-N-vinyl-2-pyrrolidone; N-vinyl-2-valerolactam; N-vinyl-2-caprolactam; and mixtures of any of the foregoing. Preferably, the N-vinyl lactam is N-vinyl-2-pyrrolidone. A comonomer such as N,N-dimethylacrylamide can be used. While other comonomers can be used without adverse results, in the present invention the majority of the monomer is an N vinyl lactam.

The crosslinking compounds found to be suitable in the present invention are multifunctional and have vinyl groups, allyl groups, and/or methallyl groups bonded to nitrogen or oxygen atoms. Exemplary compounds include divinyl, diallyl or dimethallyl esters (e.g., divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate), divinyl, diallyl or dimethallyl ethers (e.g., diethyleneglycol divinyl ether, butanediol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether), divinyl, diallyl or dimethallyl amides including bis(N-vinyl lactams), (e.g., 3,3'-ethylidene bis(N-vinyl-2-pyrrolidone)), and divinyl, diallyl or dimethallyl ureas. Presently preferred crosslinking compounds are divinyl adipate, 3,3'-ethylidene bis(N-vinyl-2-pyrrolidone), and diethyleneglycol divinyl ether.

In a preferred embodiment, the adhesive composition is a swellable, cohesive crosslinked polymeric matrix prepared by free radical polymerization of a precursor comprising N-vinyl-2-pyrrolidone monomer and less than 0.5 percent (by weight of the monomer) of 3,3'-ethylidene bis(N-vinyl-2- pyrrolidone) and a plasticizer containing a mixture of glycerol and water.

Another aspect of the invention relates to a polymerizable precursor useful in preparing hydrophilic, pressure sensitive adhesive compositions comprising a mixture of an N-vinyl lactam monomer as the major monomeric component, a plasticizer, a multi-ethylenically unsaturated compound wherein the ethylenic groups are vinyl, allyl and/or methallyl groups which are bonded to nitrogen or oxygen atoms, and a free radical initiator.

The present invention further relates to the adhesive compositions of the present invention described above further comprising an electrolyte in an amount sufficient to render the adhesive susceptible to the passage of electric current and to the use of such electrically-conductive adhesives to prepare biomedical electrodes.

According to the present invention, a disposable biomedical electrode can be made. The electrode comprises an electrical conductor, means for connecting the electrical conductor to a lead wire of an electromedical device, and an electrically conductive pressure sensitive adhesive as described above. A major portion of a major surface of the electrical conductor contacts the adhesive.

Adhesive articles such as medical tapes and dressings manufactured using the adhesive compositions of the present invention are further features of this invention.

The biomedical electrode and the electrically-conductive adhesive compositions according to the present invention offer several advantages over previously described biomedical electrodes. Foremost, the use of an N-vinyl lactam such as N-vinyl-2-pyrrolidone as the majority of the monomer and one or more of the multi-ethylenically unsaturated crosslinking compounds described above yields adhesives having excellent adhesion, cohesion, compliance and elasticity as are required of pressure-sensitive adhesives. In particular, the cohesion of the adhesive allows a clean release from skin. Glycerol, the humectant of choice for biomedical applications can be used. Further, the hydrophilic polymer of the present invention has an excellent shelf life, unlike a hydrophilic polymer based on acrylic acid. This improved shelf life is believed to result from a very low level of reaction between the polyol and the lactam to further crosslink the polymer and thereby reduce or eliminate its adhesive properties.

This invention further relates to a method of preparing an adhesive composition as described above comprising:

a) preparing a precursor comprising an N-vinyl lactam monomer, a multi-ethylenically unsaturated crosslinking compound wherein the ethylenic groups are vinyl groups, allyl groups, or methallyl groups bonded to nitrogen or oxygen atoms, a plasticizer which plasticizer is a solvent for the N-vinyl lactam monomer and the multi-ethylenically unsaturated compound, and a free radical initiator;

b) depositing the mixture on a substrate to form a layer; and c) exposing the layer to sufficient energy to initiate a free radical polymerization;

wherein the multi-ethylenically unsaturated compound and the plasticizer are present in amounts sufficient to yield a swellable cohesive polymeric matrix which is pressure-sensitive adhesive. The method is an essentially solventless method for the preparation of a layer of the adhesive of this invention because the use of a plasticizer as a solvent for N-vinyl lactam monomer and multi-ethylenically unsaturated crosslinker eliminates the need to remove solvent from the adhesive after polymerization of the monomers.

DETAILED DESCRIPTION OF THE INVENTION

Figure 1:
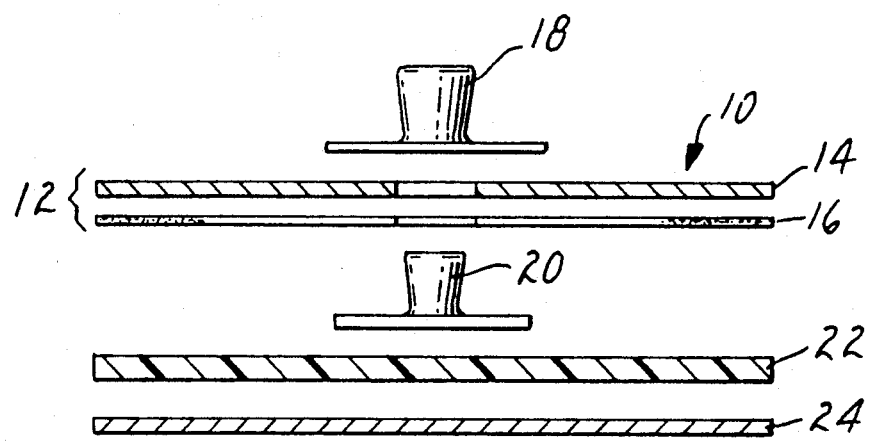
FIG. 1 is an exploded sectional view of a disposable ECG electrode containing the conductive adhesive of the invention.

The pressure-sensitive adhesive compositions of the present invention are obtained by the free-radical polymerization, either in bulk or in solution, of a precursor containing an N-vinyl lactam monomer and a crosslinking compound The polymerization can be dried and thereafter swelled with the plasticizer to make the pressure sensitive adhesive Preferably, the plasticizer is incorporated into the precursor so that evaporation of solvent and subsequent swelling with plasticizer are not necessary.

As examples of N-vinyl lactams which may be employed, the following are illustrative:

N vinyl-2-pyrrolidone,
5-methyl-N-vinyl-2-pyrrolidone,
5-ethyl-N-vinyl-2-pyrrolidone,
3,3-dimethyl-N-vinyl-2-pyrrolidone,
3-methyl-N-vinyl-2-pyrrolidone,
3-ethyl-N-vinyl-2-pyrrolidone,
4-methyl-N-vinyl-2-pyrrolidone,
4-ethyl-N-vinyl-2-pyrrolidone,
N-vinyl-2-valerolactam, and
N-vinyl-2-caprolactam The amount of N-vinyl lactam monomer in the polymerizable compositions of the present invention is generally from 5 to 50 percent by weight of the precursor and preferably about 25 to 35 percent by weight of the precursor. The N-vinyl lactam monomer (or a mixture of N-vinyl lactams) comprises a majority of the monomers present in the precursor. Preferably the N-vinyl lactam monomer(s) comprises 70 to 100 percent by weight of the noncrosslinking monomers present in the precursor, and most preferably 90 to 100 percent by weight of the noncrosslinking monomers present in the precursor. Small amounts of other monomers which are soluble in the precursor, for example, acrylic acid, methacrylic acid or hydroxyethyl methacrylate, may be included in the precursor. The most preferred pressure sensitive adhesives are provided when virtually all of the noncrosslinking monomer is N-vinyl-2-pyrrolidone.

The precursor is further comprised of a "crosslinking compound" which is a multi-ethylenically unsaturated compound wherein the ethylenic groups are vinyl groups, allyl groups, or methallyl groups, which groups are bonded to nitrogen or oxygen atoms. (As used herein, the terms "vinyl groups, allyl groups, and methallyl groups" include substituted groups; for example, the term "vinyl groups" includes isopropenyl groups.) Although the most readily available crosslinking compounds contain ethylenic groups from only one of the foregoing categories, it will be understood that crosslinking compounds having more than one of the foregoing ethylenic categories are also suitable. Although the exact level for optimum performance will vary depending upon the specific compound used, a relatively low level of crosslinking compound has been found suitable to obtain adhesives which are very tacky and yet show good release from skin. The crosslinked polymeric matrix in the adhesives of this invention have been found to be stable over long storage periods. Without being limited to any theory, no further crosslinking of the copolymer is believed to occur during long-term storage or use of the adhesive under ambient conditions. The adhesives are also very hydrophilic and readily absorb and hold water and water-soluble materials.

The crosslinking compounds found to be suitable in the invention are multifunctional and have vinyl groups, allyl groups, and/or methallyl groups bonded to nitrogen or oxygen atoms. Exemplary compounds include divinyl, diallyl or dimethallyl esters (e.g., divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate), divinyl, diallyl or dimethallyl ethers (e.g., diethyleneglycol divinyl ether, butanediol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether), divinyl, diallyl or dimethallyl amides including bis(N-vinyl lactams), (e.g., 3,3'-ethylidene bis(N-vinyl-2-pyrrolidone)), and divinyl, diallyl or dimethallyl ureas. Presently preferred crosslinking compounds are divinyl adipate, 3,3'-ethylidene bis(N-vinyl-2-pyrrolidone), and diethyleneglycol divinyl ether.

The bis(N-vinyl-lactams) can be used at lower levels than some of the other crosslinkers. Polyfunctional crosslinking agents such as tri- and tetra-functional compounds can also be used, e.g., trivinyl glyceryl ether. Such agents would be used at slightly lower levels than the difunctional crosslinking agents. However, multifunctional acrylate compounds have been found unsuitable as crosslinking compounds when the N-vinyl lactam comprises the majority of the monomeric species used in the adhesive in this invention.

The level of crosslinking compound in the adhesives of the invention will generally be between about 0.02 and about 5.0 percent by weight of the N-vinyl lactam monomer in the composition. These levels generally provide an amount of crosslinking suitable for a pressure sensitive adhesive. However, different classes of the crosslinking compounds are preferably used at different levels. The bis(N-vinyl lactams), other divinyl amides, and divinyl ureas are preferably used at levels of from about 0.02 percent to about 0.5 percent by weight of the polymer. The divinyl ethers are preferably used at levels of from about 0.5 to about 5 percent by weight of the polymer. The divinyl, diallyl or dimethallyl esters, the diallyl or dimethallyl ethers, the diallyl or dimethallyl amides, and the diallyl or dimethallyl ureas are preferably used at levels of from about 0.05 to about 2 percent by weight of the polymer. The compositions of the invention can be optimized by varying parameters such as the amount of light used to initiate polymerization, the amount of initiator, temperature, the ratios of reactants and the like.

The compositions of this invention contain a plasticizer for the crosslinked polymer. Preferred plasticizers are glycerol and mixtures of glycerol and water. Glycerol is the preferred plasticizer of the invention because it provides compositions having good adhesion to skin, it functions as a humectant to prevent excessive evaporation of moisture from the final composition, and it is less irritating than other polyol plasticizers such as ethylene glycol, propylene glycol and the like. However, these other polyols as well as alcohols (e.g., methanol, ethanol and isopropanol), ether alcohols (e.g., glycol ethers and polyethylene glycol), and any other well-known plasticizers which can swell the polymeric matrix but which do not cause skin irritation may be used either alone or in admixture with glycerol or any other plasticizer compound. Other well-known plasticizers could also be used for applications where toxicity, flammability, etc. are not concerns, such as for nonmedical applications.

The plasticizer is added in an amount sufficient to render the crosslinked copolymer pressure-sensitive adhesive. In general, the amount of plasticizer will range from about 35 to about 95 weight percent of the adhesive composition, and preferably from about 50 to about 90 weight percent. Glycerol is used in an amount up to 100% of the plasticizer and is preferably 10% to 80% of the plasticizer. When the adhesive compositions of the invention are used in bioelectrodes, water, at a concentration by weight of from about 20% to about 100%, and preferably at least about 30% by weight of the plasticizer, is used.

Additives can be included. For example, when the adhesive composition is to be used in an electrode, water and an electrolyte may be added to the precursor or the final composition. When the additive interferes with or is affected by the polymerization it can be added after polymerization. Ionic salts dissolved in the compositions to provide conductivity can be those generally used in the art for such purposes such as lithium chloride, sodium citrate and, preferably, potassium chloride. Alternatively a redox couple such as a mixture of ferric and ferrous salts such as sulfates or gluconates may be added. The amounts of these ionic salts are relatively small, from about 0.5 to 10 percent by weight of the adhesive, and preferably 1 to 4 percent.

When a redox couple, e.g., ferric and ferrous sulfates, is used the electrode can recover from an overload potential. An electrochemically inert sensing element can be used as disclosed in U.S. Pat. No. 4,846,185 (Carim) and incorporated herein by reference.

The adhesive compositions of the present invention may be used in drug delivery systems such as transdermal drug delivery systems. In such an instance, the pharmaceutical or drug to be delivered is merely compounded with the adhesive during or after its preparation. For example, if the pharmaceutical is not adversely affected by the polymerization conditions, it can be mixed into the polymerizable composition before polymerization. Otherwise, the pharmaceutical can be compounded with the adhesive after polymerization.

The polymerization of the polymer precursor is carried out by employing initiators which generate free-radicals upon the application of activating energy, such as those conventionally used in the polymerization of ethylenically unsaturated monomers. Included among useful free-radical initiators are the thermally activated initiators such as organic peroxides, organic hydroperoxides, and azo compounds. Representative examples of such initiators include benzoyl peroxide, tertiary-butyl perbenzoate, diisopropyl peroxydicarbonate, cumene hydroperoxide, azobis(isobutyronitrile), and the like. Generally, from about 0.1 to 5 percent by weight (based on the polymerizable components) of thermal initiator is used. When thermally activated initiators are employed, the polymerization is carried out at between about 40° and 100° C. for about 5 to 500 minutes, depending upon the temperature and the composition of the polymerizable composition.

However, the presently preferred polymerization initiators are activated photochemically. Such photochemically activated initiators are well known and have been described in the polymerization art, e.g., Chapter II of "Photochemistry" by Calvert and Pitts, John Wiley and Sons (1966) and in Progress in Organic Coatings, 13 (1985) 123-150. Representative examples of such initiators include acyloins and related compounds such as benzoin, benzoin methyl ether, benzoin ethyl ether, benzoin isopropyl ether, benzoin isobutyl ether, α-methylbenzoin, and 2-hydroxy-2-methyl-1-phenyl-1-propanone; and benzilketals such as benzildimethylketal and benzildiethylketal. A presently preferred photoinitiator is 2-hydroxy-2-methyl-1-phenyl-1-propanone.

Generally, the photoinitiator is used in amounts ranging from about 0.01 to 5 percent by weight of monomer. Preferably, about 0.02 to 2.0 percent by weight of photoinitiator is used. When the activating energy is ultraviolet light, the irradiation is typically initiated at a temperature in the range of 0° to 50° C. for 0.5 minutes to 5 hours or more depending upon the intensity of the radiation and the opacity of the adhesive.

It will be appreciated that other methods of initiating free radical polymerization are well known and may be used in the practice of the present invention. For example, systems involving the chemical reaction of two or more species to generate a free radical initiator may be employed.

There are several ways of preparing the pressure sensitive adhesive compositions of the present invention. The variations include polymerizing the polymer precursor in bulk or solution, with or without plasticizer present. The adhesive is preferably prepared by the essentially solventless process of polymerizing a precursor comprising an N-vinyl lactam monomer, a crosslinker, an initiator and a plasticizer in which the monomer and crosslinker are soluble. Alternatively, a solvent can be added to facilitate mixing and polymerization of the mixture and then removed, e.g., by evaporation. The precursor can be coated on an electrode plate or a transfer sheet, and depending on the free radical initiator, exposed to sufficient energy, e.g., either heat or actinic radiation, to result in the formation of a swellable cohesive crosslinked copolymer. The adhesive layer is generally between about 5 and 100 mils (0.13 mm to 2.54 mm) thick with approximately 35 mil (0.89 mm) being preferred.

A better understanding of the bioelectrode of the invention will be facilitated by reference to the accompanying drawings.

Referring to FIG. 1, a disposable ECG electrode 10 is illustrated in which the electrically active conductor 12 is provided by a film 14 approximately 1 3/16 inches in diameter which has been vapor coated with silver 16 on its lower surface. The electrically active conductor 12 contacts a standard stud/eyelet connector which is used to connect the electrode to an electromedical instrument, e.g., an electrocardiograph. In the embodiment illustrated, stud 18 is made of stainless steel and eyelet 20 is formed of plastic having a conventional silver/silver chloride coating. Conductive adhesive layer 22 incorporates an ionic salt (see, e.g., example 24 below). It is approximately 28 mils thick and covers the lower, skin-directed surface of the conductor 12. A release liner 24 protects the conductive adhesive prior to use.

Figure 3:
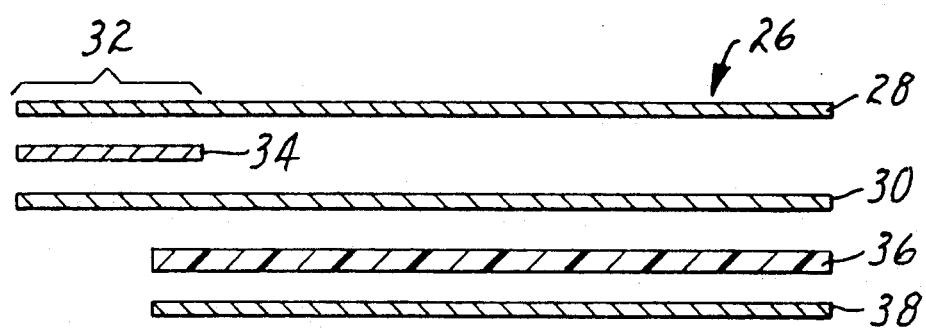
FIG. 3 is an exploded sectional view of the electrode of FIG. 2.
Figure 2:
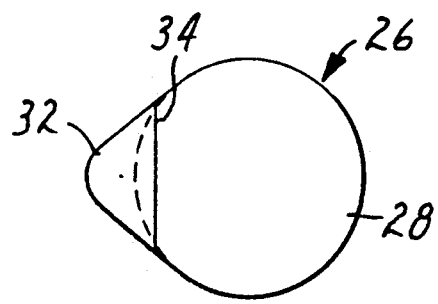
FIG. 2 is a top plan view of an alternative embodiment of the ECG electrode of FIG. 1.

The electrode 26 of FIGS. 2 and 3 comprises a circular piece of standard medical pressure-sensitive adhesive tape 28 such as Micropore ™ tape sold by the 3M Company, Saint Paul, MN. Adhesive tape 28 is laminated to a disc of tin foil 30 approximately 1.7 mils thick and 1 ¼ inches in diameter. Tin foil disc 30 constitutes the electrical connector of the electrode Tab 32 extends from tape 28 and tin foil disc 30 to provide a means for connecting the electrode plate to an electrocardiograph by way of any alligator clamp (not shown) or other suitable connector. Tab 32 is reinforced with a piece of polyethylene 34 (preferably colored) so as to be readily visible to the user. Conductive adhesive layer 36, approximately 28 mils thick, is applied to the lower, skin-directed surface of tin foil disc 30. Release liner is used to protect the adhesive prior to use.

The following examples illustrate the adhesives of this invention. All parts are by weight unless otherwise noted. The crosslinking agents are identified as follows:

| Crosslinking Agent | Compound |
| --- | --- |
| A | diethyleneglycol divinyl ether |
| B | butanediol divinyl ether |
| C | divinyl adipate |
| D | 3,3'-ethylidene bis(N-vinyl-2-pyrrolidone) |
| E | pentaerythritol diacrylate |
| F | triethyleneglycol dimethacrylate |
| G | ethyleneglycol dimethacrylate |
| H | diallyl maleate |
| I | diallyl succinate |
| J | dimethallyl maleate |
| K | diallyl urea |

EXAMPLE 1

A mixture of 25 g of N-vinyl-2-pyrrolidone, 41.5 g of glycerol, 10.5 g of water, 0.4 g of Crosslinking Agent A (diethyleneglycol divinyl ether) and 0.25 g of 2-hydroxy-2-methyl-1-phenyl-1-propanone was cast onto a silicone coated poly(ethylene terephthalate) release liner such as those described in U.S. Pat. No. 4,386,135 supported on a glass slide within the space surrounded by two gaskets of poly(tetrafluoroethylene) having a total thickness of 0.86 mm. The mixture was then covered with a quartz plate covered with a second silicone coated poly(ethylene terephthalate) release liner. The plate and slide were clamped together and irradiated with UV light placed at a distance of 35 cm for 10-15 minutes. The resulting gel was clear, extremely tacky and gave clean release from skin.

EXAMPLES 2-3 and COMPARATIVE EXAMPLES A-D

Variation of Crosslinking Agent

Using the method of Example 1, the adhesives shown in Table I were prepared using the components shown below.

TABLE I

| Ex. | N-Vinyl-2-pyrrolidone (g) | Glycerol (g) | Water (g) | Photoinitiator (g) | Crosslinking Agent (g) |
| --- | --- | --- | --- | --- | --- |
| 2 | 5.0 | 8.3 | 2.1 | 0.05 | A (0.05) |
| 3 | 5.0 | 8.3 | 2.1 | 0.05 | B (0.05) |
| A | 5.0 | 8.3 | 2.1 | 0.05 | E (0.08) |
| B | 5.0 | 8.3 | 2.1 | 0.05 | F (0.09) |
| C | 5.0 | 8.3 | 2.1 | 0.05 | G (0.05) |
| D | 5.0 | 8.3 | 2.1 | 0.05 | G (0.15) |

In each Example, the thickness of the adhesive layer was 34 mil.

Both Examples 2 and 3 provided excellent adhesives which are observed to be readily and cleanly removed from human skin. The adhesive from Comparative Example A was very tacky and left a slight residue on skin. The adhesive from Comparative Example B was very tacky, stuck to the release liner and tended to be stringy. The adhesive of Comparative Example C was clear with good tack but left a slight residue on skin. The adhesive of Comparative Example D was slightly milky, stiffer, flowed under tensile deformation, and did not separate cleanly, leaving a substantial residue on skin.

EXAMPLES 4-7

Variation of Level of Crosslinking Agent

Using the method and amounts of Example 2, the amount of Crosslinking Agent A (diethyleneglycol divinyl ether) was varied while maintaining other variables constant to examine the variation of properties of the adhesive as shown in Table II.

TABLE II

| Example | Amount of Crosslinking Agent (g) | Properties of Adhesive |
|---------|----------------------------------|------------------------|
| 4 | 0.025 | clear adhesive, soft and tacky, stringy release |
| 5 | 0.05 | clear adhesive, very tacky, clean release |
| 6 | 0.10 | clear adhesive, very tacky, clean release (slightly better than Example 5) |
| 7 | 0.20 | slightly less tacky, slightly stiffer than Examples 5 and 6, clean release |

EXAMPLES 8 and 9

Adhesive with Increased Water Content

A reaction apparatus consisting of one glass plate (lower) and one quartz plate (upper) covered with poly(ethylene terephthalate) coated with silicone release agent and two stacked, identical concentric poly(tetrafluoroethylene) gaskets of about 34 mil total thickness and encircling an area of about 594 $cm^2$ was filled with the reaction mixtures A piece of hexagonally patterned scrim of polypropylene, was set into the reaction mixture before irradiation with UV light The apparatus was irradiated from the top for 15 minutes with UV light at a distance of about 30 centimeters. The mixtures are shown in Table III. The photoinitiator was 2-hydroxy-2-methyl-1-phenyl-1-propanone.

TABLE III

| Ex. | N-vinyl-2-pyrrolidone (g) | Glycerol (g) | Water (g) | Photoinitiator (g) | Crosslinker (g) |
|-----|---------------------------|--------------|-----------|--------------------|-----------------| 
| 8 | 80 | 91.2 | 75.2 | 0.8 | C (0.18) |
| 9 | 40 | 45.6 | 37.6 | 0.4 | A (0.8) |

The resulting pressure sensitive adhesive gels were very tacky, but released cleanly from skin.

EXAMPLES 10-18

The adhesives prepared in these Examples were run on a belt coating machine at various web speeds. Two layers of release-agent coated poly(ethylene terephthalate) were fed onto a moving air-cooled web as the mixture to be polymerized was knife-coated between the layers This layered composition was fed through a bank of fluorescent lamps with 90% of the emitted light between 300 and 400 nanometers. (Example 12 was run with only half of the lights of the apparatus in operation)

A 30 mil thick adhesive layer was provided The light intensity was measured by a light meter (a Dynachem UV integrating Radiometer Model 500, Dynachem Corp., Tustin, CA). The web speeds are shown in Table IV on a relative basis, where 400 equals 5.6 feet per minute, down to 50 equals 0.7 feet per minute The various adhesives prepared are shown in Table IV. The photoinitiator used was 2-hydroxy-2-methyl-1-phenyl-1-propanone

TABLE IV

| Example | N-Vinyl-2-pyrrolidone (g) | Glycerol (g) | Water (g) | Photoinitiator (g) | Crosslinking Agent (g) | Web Speed |
|---------|---------------------------|--------------|-----------|--------------------|------------------------|-----------|
| 10 | 32.5 | 54 | 13.7 | 0.32 | C (0.13) | 400 |
| 11 | 32.5 | 54 | 13.7 | 0.32 | C (0.13) | 200 |
| 12 | 32.5 | 54 | 13.7 | 0.32 | C (0.13) | 400 |
| 13 | 100 | 166 | 42 | 1.0 | A (1.6) | 400 |
| 14 | 100 | 166 | 42 | 1.0 | A (1.6) | 200 |
| 15 | 100 | 166 | 42 | 1.0 | A (1.6) | 100 |
| 16 | 100 | 166 | 42 | 1.0 | A (1.6) | 50 |
| 17 | 16 | 26 | 6.8 | 0.32 | A (0.26) | 400 |
| 18 | 16 | 26 | 6.8 | 0.32 | A (0.26) | 100 |

The compositions of Examples 10, 11, 12 and 16 provided adhesive that was clear, very tacky and released cleanly, without residue, from human skin. The compositions of released in a stringy fashion The adhesive of Example 15 was clear, tacky and released leaving little or no residue. The adhesives of Examples 17 and 18 were clear and tacky and released in a stringy fashion.

EXAMPLE 19

A mixture of 5.0 g of N-vinyl-2-pyrrolidone, 8.3 g of glycerol, 2.1 g of water, 0.005 g of Crosslinking Agent D (3,3'-ethylidene bis-(N-vinyl-2-pyrrolidone)) and 0.05 g of 2 hydroxy-2-methyl-1-phenyl-1-propanone was photolyzed according to the method of Example 1 to give a clear gel. The gel was tacky and left no residue on the skin.

EXAMPLE 20

A mixture of 5 g N-vinyl-2-pyrrolidone, 8.3 g of glycerol, 2.1 g of water, 0.005 g Crosslinking Agent H (diallyl maleate) and 0.05 g of 2-hydroxy-2-methyl-1-phenyl-1-propanone was photolyzed according to the method of Example 1. This procedure yielded a clear, tacky gel that released cleanly from skin.

EXAMPLE 21

Example 20 was repeated with the exception that 0.010 g of Crosslinking Agent I (diallyl succinate) was substituted for the 0.005 g of Crosslinking Agent H. The resulting gel was clear and tacky, yet it released cleanly from skin.

EXAMPLE 22

Example 20 was repeated with the exception that 0.010 g of Crosslinking Agent J (dimethallyl maleate) was substituted for the 0.005 g of Crosslinking Agent H. The resulting clear, tacky gel released cleanly from skin.

EXAMPLE 23

Example 20 was repeated with the exception that 0.010 g of Crosslinking Agent K (1,3-diallylurea) was substituted for the 0.005 g of Crosslinking Agent H. The resulting clear, tacky gel released cleanly from skin.

EXAMPLE 24

A mixture of 44 g water, 25 g glycerol, 30 g N-vinyl-2-pyrrolidone, 0.15 g 2-hydroxy-2-methyl-1-phenyl-1-propanone, 0.052 g 3,3'-ethylidene bis(N-vinyl-2-pyrrolidone) and 1 g potassium chloride was prepared. A portion of this solution was poured onto a silicone coated release liner covered with a nylon screen material. The sample was allowed to sit in a nitrogen atmosphere for 1 minute and was then photolyzed for 7 minutes with two sun lamps. The light entered the nitrogen purge chamber through a quartz window from a distance of 12 inches. The resulting tel was very tacky.

COMPARISON EXAMPLES E-H

Experiments were performed using precursors having varying amounts of N-vinyl-2-pyrrolidone (NVP) and acrylic acid (AA) as a comonomer. Rather than use one of the crosslinkers of the present invention, triethylene glycol bis-methacrylate (TEGBM) was used. Each 100 g precursor contained 1.0 g KCl, 25.5 g H$_2$O, NaOH (in an amount sufficient to neutralize 50% of the acid groups), 0.07 g benzildimethylketal, 0.125 g TEGBM, acrylic acid (AA), N-vinyl-2-pyrrolidone (NVP) and glycerol (balance). the precursor was made by adding the KCl to water in a glass container and stirring until the salt dissolved. The NaOH was added and dissolved. Thereafter the glycerol was added. In a separate container the acrylic acid (if any) was mixed with the initiator (benzildimethylketal) and the crosslinker (TEGBM). The two mixtures were mixed and just prior to coating on a substrate the NVP was added. The precursor was coated on a substrate and exposed to UV radiation in a nitrogen atmosphere for a time sufficent to complete polymerization. Immediately following polymerization the composition was inspected for opacity (indicating phase separation) and for initial tack. Examples E and F showed acceptable tack and no phase separation. Example G was soft and left a residue when removed from skin Example H was very soft and left considerable residue when removed from skin.

TABLE V

| Example | AA (%) | NVP (%) |
| --- | --- | --- |
| E | 16.87 | 5.62 |
| F | 12.5 | 12.5 |
| G | 6.87 | 20.62 |
| H | 0 | 30 |

The present invention may be embodied in other specific forms without departing from its spirit or essential characteristics. The described embodiments are to be considered in all respects only as illustrative and not restrictive The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A hydrophilic, pressure-sensitive adhesive composition, comprising:
   a crosslinked, swellable polymeric matrix formed by a free-radical polymerization of at least one polymerizable monomeric species wherein a majority of the polymerizable monomeric species is comprised of one or more N-vinyl lactams, and a crosslinker which is a multi-ethylenically unsaturated compound selected from the group consisting of dinvinyl succinate, dinvinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, dimethallyl adipate, diethyleneglycol divinyl ether, butanediol divinyl ether, ethylene glycol divinyl ether, ethylene glycol diallyl ether, diethylene glycol diallyl ether, butane diol diallyl ether ethylene glycol dimethallyl ether, diethylene glycol dimethallyl ether, butane diol dimethallyl ether, 3,3'-ethylidene bis(N-vinyl-2-pyrrolidone), and 1,3-diallyl urea,
   said crosslinker present in an amount from about 0.02 to about 2 percent by weight of the polymerizable monomer species; and
   a plasticizer;
   wherein the plasticizer is present in an amount sufficient for the composition to be cohesive, swellable and pressure-sensitive adhesive.

2. A composition in accordance with claim 1 wherein said multi-ethylenically unsaturated compound is 3,3'-ethylidene bis(N-vinyl-2-pyrrolidone) and is present in an amount of from about 0.02 to about 0.5 percent by weight of the polymerizable monomeric species.

3. A composition in accordance with claim 1 wherein said multi-ethylenically unsaturated compound is divinyl succinate, dinvinyl adipate, dinvinyl maleate, divinyl, oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, dimethallyl adipate, ethylene glycol diallyl ether, diethylene glycol diallyl ether, butane diol diallyl ether, tethylene glycol dimethallyl ether, diethylene glycol dimethallyl ether, butane diol dimethallyl ether, or 1,3-diallyl urea; and
   wherein said multi-ethylenically unsaturated compound is present in an amount of from about 0.05 to about 2 percent by weight of the polymerizable monomeric species.

4. A composition in accordance with claim 1 wherein said multi-ethylenically unsaturated compound is diethyleneglycol divinyl ether, butanediol divinyl ether, or ethylene glycol divinyl ether; and
   wherein said multi-ethylenically unsaturated compound is present in an amount from about 0.5 to about 2 percent by weight of the polymerizable monomeric species.

5. A composition in accordance with claim 2 wherein the N-vinyl lactam monomer is N-vinyl-2-pyrrolidone.

6. A composition in accordance with claim 1 wherein the plasticizer is comprised of glycerol.

7. A composition in accordance with claim 1 wherein said plasticizer is comprised of glycerol and water.

8. A composition in accordance with claim 1 wherein the plasticizer is present in an amount of at least 35 percent by weight of the composition.

9. A composition in accordance with claim 1 wherein said free-radical polymerization is initiated photochemically.

* * * * *

UNITED STATES PATENT AND TRADEMARK OFFICE
CERTIFICATE OF CORRECTION

PATENT NO. : 5,225,473
DATED : July 6, 1993
INVENTOR(S) : Daniel C. Duan

Page 1 of 3

It is certified that error appears in the above-indentified patent and that said Letters Patent is hereby corrected as shown below:

Col. 1, line 61, delete " mers' " and insert --mers--.

Col. 1, line 63, after "least 15% of the" insert --monomers to be water soluble. In U.S. Patent No. 4,352,359--.

Col. 2, line 7, after "α," delete space.

Col. 2, line 8, delete "Engle" and insert --Engel--.

Col. 3, line 6, delete "5%" and insert --15%--.

Col. 3, line 64, delete "The N vinyl" and insert --The N-vinyl--.

Col. 4, line 9, delete "The N vinyl" and insert --The N-vinyl--.

Col. 4, line 4, delete "N-vinyl-2- pyrrolidone" and insert --N-vinyl-2-pyrrolidone--.

Col. 5, line 61, insert --.-- after "compound" and before "The".

Col. 5, line 63, insert a --.--, after "adhesive".

Col. 6, line 1, delete "N vinyl-2-pyrrolidone" and insert --N-vinyl-2-pyrrolidone--.

UNITED STATES PATENT AND TRADEMARK OFFICE
CERTIFICATE OF CORRECTION

PATENT NO. : 5,225,473
DATED : July 6, 1993
INVENTOR(S) : Daniel C. Duan

It is certified that error appears in the above-indentified patent and that said Letters Patent is hereby corrected as shown below:

Col. 9, line 55, insert -- . -- after "electrode" and before "Tab".

Col. 11, line 34, insert -- . -- after "mixtures" and before "A".

Col. 11, line 58, insert -- . -- after "layers" and before "This".

Col. 11, line 63, insert -- . -- after "provided" and before "The".

Col. 12, line 21, after "compositions of" insert --Examples 13 and 14 provided clear tacky adhesive which--.

Col. 12, line 30, delete "2 hydroxy-2-methyl" and insert --2-hydroxy-2-methyl--.

Col. 13, line 6, delete "tel" and insert --gel--.

Col. 13, line 18, delete "the" and insert --The--.

Col. 13, line 33, insert -- . -- after "skin" and before "Example".

Col. 13, line 47, insert --. -- after "restrictive" and before "The".

Col. 13, lines 58-59, delete "of the polymerizable monomeric species is comprised" and insert --of the monomeric component is comprised--.

UNITED STATES PATENT AND TRADEMARK OFFICE
CERTIFICATE OF CORRECTION

PATENT NO. : 5,225,473
DATED : July 6, 1993
INVENTOR(S) : Daniel C. Duan

It is certified that error appears in the above-indentified patent and that said Letters Patent is hereby corrected as shown below:

Col. 14, line 9, delete "diallyl ether ethylene" and insert --diallyl ether, ethylene--.

Col. 14, line 29, delete " , " after "divinyl".

Col. 14, line 37, delete "tethylene glycol" and insert --ethylene glycol--.

Col. 14, line 52, delete "claim 2" and insert --claim 1--.

Signed and Sealed this

Twenty-second Day of April, 1997

Attest:

BRUCE LEHMAN

*Commissioner of Patents and Trademarks*

*Attesting Officer*